United States Patent [19]
Fujimura et al.

[11] Patent Number: 5,489,609
[45] Date of Patent: Feb. 6, 1996

[54] 2-AMINOETHANESULFONIC ACID ZINC COMPLEX COMPOUND

[75] Inventors: Hajime Fujimura, Kyoto; Takahiro Yabuuchi, Takarazuka; Teruo Tanaka, Kyoto; Yoichi Nagamura, Toyoake, all of Japan

[73] Assignee: Zaidan Hoijn Seisan Kaihatsu Kagaku Kenkyusho, Kyoto, Japan

[21] Appl. No.: 356,305

[22] PCT Filed: Jun. 14, 1993

[86] PCT No.: PCT/JP93/00813

§ 371 Date: Dec. 15, 1994

§ 102(e) Date: Dec. 15, 1994

[87] PCT Pub. No.: WO93/25558

PCT Pub. Date: Dec. 23, 1993

[30] Foreign Application Priority Data

Jun. 18, 1992 [JP] Japan ................. 4-186090

[51] Int. Cl.$^6$ .................. A61K 31/315; C07F 3/06
[52] U.S. Cl. .................. 514/494; 514/894; 514/925; 556/118; 556/119; 556/130
[58] Field of Search ................. 556/118, 119, 556/130; 514/494, 894, 925

[56] References Cited

U.S. PATENT DOCUMENTS 4,355,043  10/1982  Durlach ................. 424/289

FOREIGN PATENT DOCUMENTS 0206692  12/1986  European Pat. Off. .
93014095  7/1993  WIPO .

OTHER PUBLICATIONS

Chemical Abstracts, vol. 88, No. 4, Jan. 23 1978, Abstract No. 30369m, p. 477.

*Primary Examiner*—Porfirio Nazario-Gonzales
*Attorney, Agent, or Firm*—Burgess, Ryan & Wayne

[57] ABSTRACT

The present invention covers 2-aminoethanesulfonic acid zinc complex compound as represented by the formula [I]:

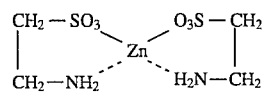

as well as a process for producing the same, and an anti-hepatitis agent, liver function improving agent and anti-ulcer agent. As compared with 2-aminoethanesulfonic acid, glutathione and glycyrrhizin, the compound (I) of the present invention exhibits improved anti-hepatitis activity, and also strengthens detoxicating activity toward various compounds to thereby develop liver function improving activity, while the said compound shows excellent anti-ulcer activity but greatly lowered toxicity.

6 Claims, No Drawings

2-AMINOETHANESULFONIC ACID ZINC COMPLEX COMPOUND

CROSS REFERENCE TO RELATED APPLICATION

This aplication is a request for U.S. Examination under 35 U.S.C. §371 of International application No. PCT/JP93/00813 filed on Jun. 14, 1993.

1. Technical Field

The present invention relates to a novel 2-aminoethanesulfonic acid zinc complex compound, to a process for producing the same and to an anti-hepatitis agent, liver function improving agent and anti-ulcer agent which individually contain the same as an active ingredient.

2. Background Art

2-Aminoethanesulfonic acid (taurine) is already known to possess liver function protecting activity, but with its weak activity, cannot be expected to find application as an excellent anti-hepatitis agent and liver function improving agent.

The present inventors, with a specific view to preparing improved pharmaceuticals based on 2-aminoethanesulfonic acid derivatives, have conducted intensive testing for their pharmacological activities. In the course of this, it was discovered that the reaction of 2-aminoethanesulfonic acid with an alkali agent and zinc compound can yield [bis(2-aminoethanesulfonic acid).bis(alkali 2-aminoethanesulfonate)]zinc as represented by the following formula (Japanese Patent Application No. Hei 4-24642 (1992):

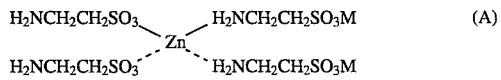
(A)

(wherein M is an alkali metal).

The compounds of the formula (A), which possess greater antihepatitis activity, liver function improving activity and antiulcer activity than 2-aminoethanesulfonic acid, still show relatively reduced zinc contents as low as 10.76 and 10.21% in the cases of M being sodium and potassium, respectively. In the light of the above, the inventors carried out further research and synthesized bis(2-aminoethanesulfonic acid)zinc with a zinc content of 20.85%. Pharmacological tests indicate that the zinc complex compound, when compared with the compounds of the formula (A), exhibits more markedly potent anti-ulcer activity as well as comparable anti-hepatitis and liver function improving activities, and the finding was followed by additional research, leading to the completion of the present invention.

DISCLOSURE OF THE INVENTION

The present invention relates to a 2-aminoethanesulfonic acid zinc complex compound represented by formula [I]:

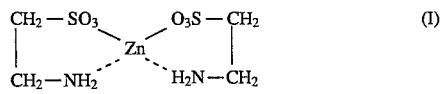
(I)

and to a process for producing the same as well as to an antihepatitis agent, liver function improving agent and anti-ulcer agent.

The compound of formula (I) can be produced by reacting a zinc compound (0.5 mole) with an alkali metal 2-aminoethanesulfonate (1 mole).

The alkali metal 2-aminoethanesulfonate can be prepared by reacting 2-aminoethanesulfonic acid (1 mole) with an alkali agent (1 mole). The resultant alkali metal salt may be reacted with the zinc compound after being isolated, but can also be reacted with the zinc compound as such without being isolated.

As the alkali agent, there can desirably be used alkali metal alcoholates, such as sodium methylate, sodium ethylate, potassium methylate, potassium ethylate or potassium t-butoxide.

Referring to the zinc compound, zinc bromide and zinc iodide are preferred, but other zinc compounds may be utilized.

The reaction of the zinc compound with the alkali metal 2-aminoethanesulfonate is normally conducted in a suitable solvent, such as methanol and ethanol, at room temperature or under warming for several hours, and after conclusion of the reaction, the reaction product can be purified by conventional means.

The compound of formula (I) possesses improved anti-hepatitis, liver function improving and anti-ulcer activities, and shows reduced toxicity, thus being useful as an anti-hepatitis, liver function improving and anti-ulcer agent. The compound, either per se or after being mixed with pharmacologically acceptable, appropriate excipients, carriers, diluents, etc., can be administered orally or parenterally in various dosage forms, such as tablets, capsules, powders, syrups and ointments. The compound is administered to patients at varied doses depending upon their symptoms, age, body weight, route of administration and the like, and is normally given to adult patients orally at a single dose of 50 to 200 mg, twice to three times a day.

Described below are Examples and Test Examples to illustrate the present invention in more detail.

EXAMPLE

A 11.3 g quantity of zinc bromide was dissolved in 100 ml of dried methanol, and a solution of 12.5 g (0.1 mole) of 2-aminoethanesulfonic acid and 19.3 ml (0.1 mole) of 28% sodium methylate methanol solution in 220 ml of dried methanol was added dropwise to the solution at 60° to 70° C. under stirring, followed by stirring at the same temperature for 2 hours. After the solution was cooled, the precipitate that crystallized out was recovered by filtration and washed with dried methanol to give 22.6 g (yield of 92.6%) of [bis(2-aminoethanesulfonic acid)]zinc in the form of a colorless powder. m.p. 330° C. (decomp.).

Elemental analysis (%): $C_4H_{12}N_2O_6S_2Zn$ Calcd.: C: 15.31, H: 3.86, N: 8.93, Zn: 20.85 Found: C: 15.20, H: 3.77, N: 8.64, Zn: 20.60 IR (KBr, $cm^{-1}$): 3298, 3263, 3183, 2985, 1622, 1508, 1464, 1408, 1369, 1309, 1234, 1221, 1176, 1150, 1106, 1064, 1047, 994.

Test Examples (Test compounds)

1) Bis(2-aminoethanesulfonic acid)zinc (the compound of the present invention, as hereinafter referred to briefly as "TTZ").

2) [Bis(2-aminoethanesulfonic acid).bis(2-aminoethanesulfonate)]zinc (the product of Japanese Patent application No. Hei 4-24642 (1992), hereinafter referred to briefly as "FTZ").

3) 2-Aminoethanesulfonic acid

4) Glutathione

5) Glycyrrhizin

1. Anti-hepatitis test (1) Hepatopathy in mice

A group of 8 ddy strain male mice (weighing about 30 g) kept fasting from the previous day was treated by intraperitoneal injection of 0.5% carbon tetrachloride in olive oil at a dose of 0.6 ml and thereafter allowed free access to food.

Three hours after the administration of carbon tetrachloride, the test compound suspended in powdered gum arabic was given to the animals orally at a dose of 200 mg/kg, and blood samples were drawn from the mice under anesthesia with ether through the abdominal descending aorta 24 hours after the administration of carbon tetrachloride. The collected blood was centrifuged at a rate of 3,000 rpm for 15 min, followed by measurement of the activities of aspartate transaminase (AST) and alanine transaminase (ALT) by means of the Lippie method. The results are shown in Table 1.

TABLE 1

| Test compound | AST IU, mean ± S.D. | ALT IU, mean ± S.D. |
|---|---|---|
| Treated group | 11884.2 ± 2042.1 | 12677.9 ± 828.2 |
| TTZ | 7256.9 ± 1464.7* | 8899.4 ± 927.9* |
| FTZ | 7024.7 ± 1113.4* | 8597.1 ± 1450.4* |
| 2-Amino-ethane-sulfonic acid | 12885.2 ± 2468.3 | 14609.6 ± 1684.5 |
| Glutathione | 11423.3 ± 1960.8 | 12030.2 ± 1204.5 |
| Glycyrrhizin | 12367.6 ± 1102.1 | 13362.1 ± 1753.1 |

Note:
*Level of significance $p < 0.05$

TTZ, or the compound of the present invention, exhibited significant suppressory activity equal to that of FTZ, whereas none of 2-aminoethanesulfonic acid, glutathione and glycyrrhizin that were used as controls at the same dose developed suppressory activity.

(2) Disorder of isolated liver cells

Isolated liver cells of rats were prepared by means of the Segren's collagenase irrigation method, whereby a liver cell suspension was prepared to a concentration of 6×108 liver cells/ml. Into 2 ml of the suspension placed in an Erlenmeyer flask was put a test tube of about 0.5 ml capacity containing a 25% carbon tetrachloride solution in olive oil to saturate the reaction system with carbon tetrachloride vapor, and after the flask was tightly stoppered, preincubation was carried out at 37° C. for 30 min. One ml of a solution of the test compound in Hunk's solution was added to the suspension of liver cells, while 1 ml of Hunk's solution was added to a control. After the reaction was allowed to proceed at 37° C. for 30 min, a specifically determined volume of the reaction solution was pipetted out and immediately centrifuged under 500 g for 30 seconds, and ALT and AST leached out into the supernatant liquid were determined for activity by the Lippie method. The results are shown in Table 2.

TABLE 2

| Test compound | Conc. of test soln. (mg/dl) | ALT IU mean ± S.D. | AST IU mean ± S.D. |
|---|---|---|---|
| Non-treated | | 549.5 ± 33.8 | 254.4 ± 12.9 |
| Treated group | | 1158.5 ± 136.7 | 379.1 ± 39.4 |
| TTZ | 0.1 | 525.1 ± 26.0* | 44.3 ± 11.1* |
| | 0.05 | 649.1 ± 42.4* | 68.2 ± 7.5* |
| | 0.025 | 637.2 ± 93.7* | 125.7 ± 48.2* |
| | 0.0125 | 944.7 ± 61.7* | 327.9 ± 36.6* |
| FTZ | 0.1 | 435.7 ± 25.3* | 33.5 ± 3.5* |
| | 0.05 | 389.2 ± 7.3* | 79.4 ± 12.3* |
| | 0.025 | 459.0 ± 93.8* | 186.8 ± 35.3* |
| | 0.0125 | 414.7 ± 36.2* | 198.2 ± 22.5* |
| 2-Aminoethane-sulfonic acid | 0.1 | 867.7 ± 158.8* | 318.8 ± 49.5* |
| | 0.05 | 849.1 ± 60.2* | 296.3 ± 30.5* |
| | 0.025 | 869.8 ± 87.6* | 309.8 ± 32.4* |
| | 0.0125 | 847.6 ± 60.4* | 338.8 ± 37.1* |

TABLE 2-continued

| Test compound | Conc. of test soln. (mg/dl) | ALT IU mean ± S.D. | AST IU mean ± S.D. |
|---|---|---|---|

Note:
*Level of significance $p < 0.05$

TTZ, or the compound of the present invention, exhibited suppressory activity equal to that of FTZ but clearly superior to that of 2-aminoethanesulfonic acid alone.

2. Test on liver function improvement (1) Protective activity against acetaldehyde toxicity:

Rats kept fasting with a supply of drinking water were weighed and divided into groups in such a manner that the mean body weight was uniform among the groups, with each group consisting of 10 heads. The rats were given acetaldehyde orally at a dose of 1,200 mg/kg, and the death rate within 24 hours was determined, wherein the test drug substances were administered orally 30 min before the application of acetaldehyde, with the vehicle (0.5% aqueous sodium carboxymethylcellulose) alone being given to a control group. The results are shown in Table 3.

TABLE 3

| Test drug substance | Dose (mg/kg) | No. of dead animals (n/10) | Death rate (%) |
|---|---|---|---|
| Vehicle | — | 10/10 | 100 |
| TTZ | 150 | 3/10 | 30 |
| " | 300 | 0/10 | 0 |
| FTZ | 250 | 4/10 | 40 |
| " | 500 | 2/10 | 20 |
| 2-Aminoethane-sulfonic acid | 250 | 6/10 | 60 |
| 2-Aminoethane-sulfonic acid | 500 | 5/10 | 50 |

TTZ, or the compound of the present invention, was found to exhibit distinct protective activity against the lethal toxicity of acetaldehyde at lower doses than FTZ, which activity was shown to be more potent than that of 2-aminoethanesulfonic acid.

3. Anti-ulcer test Animal used:

Used in the test as an experimental animal were 6-week aged, male rats of KBL Wistar strain that had been observed to produce no abnormalities in general conditions after being subjected to acclimatization for about one week from the purchase of the same.

(1) Stomach injury with hydrochloric acid/ethanol:

Rats weighing 193 to 228 g were kept fasting with free access to water for 24 hours before being used in the experiment. The rats were divided into groups each consisting of 8 heads in such a way that their mean body weights were nearly uniform among the groups, treated by oral administration of hydrochloric acid/ethanol (0.15 mole hydrochloric acid solution in 80% ethanol) at a dose of 5 ml/kg body weight and sacrificed through cervical vertebrae dislocation 1 hour after administration. The stomachs were removed and treated with formalin, and individual ulcers formed in the glandular portion of the stomach were measured in length (mm), with the measured ulcer lengths summed for each rat. The test compound was suspended in a 0.5% aqueous solution of sodium carboxymethylcellulose, and the suspension was given to the test group orally at a dose of 10 ml/kg body weight 30 min before administration of hydrochloric acid/ethanol, whereas the vehicle (0.5% aqueous sodium carboxymethyl-cellulose) alone was applied to a control group. The results are shown in Table 4:

TABLE 4

| Test compound | Dose (mg/kg) | Incidence of ulcer | Ulcer coefficient (mm) mean ± S.E. | Suppression % | $UD_{50}$ (mg/kg) (95% C.L.) |
|---|---|---|---|---|---|
| Vehicle (No. 1) | — | 8/8 | 47.1 ± 6.9 | — | |
| Vehicle (No. 2) | — | 8/8 | 52.5 ± 10.1 | — | |
| Vehicle (No. 3) | — | 8/8 | 36.5 ± 5.3 | — | |
| TTZ | 12.5 | 8/8 | 32.2 ± 4.9 | 11.8[c] | |
|  | 25 | 8/8 | 24.6 ± 8.8 | 63.3[b] | 22.8 |
|  | 50 | 5/8 | 2.2 ± 1.1* | 96.3[a] | (21.8–23.8) |
| FTZ | 50 | 8/8 | 30.4 ± 7.8 | 35.5[a] | |
|  | 75 | 8/8 | 30.2 ± 10.2 | 42.5[b] | 86.0 |
|  | 150 | 8/8 | 11.7 ± 4.7* | 67.9[c] | (80.6–91.7) |

Notes:
[a] Suppression in Vehicle No. 1.
[b] Suppression in Vehicle No. 2.
[c] Suppression in Vehicle No. 3
*Level of significance, P < 0.01.

(2) Stomach injury through water-immersion constraint stress:

Rats weighing 183 to 235 g were kept fasting with free access to water for 24 hours before being used in the experiment. The rats were divided into groups each consisting of 8 heads in such a way that their mean body weights were nearly uniform among the groups, stress-loaded by soaking the animals placed in a stress cage of Univ. of Tokyo type in a water tank at 23° C. up to the xiphoid and then sacrificed through cervical vertebrae dislocation 7.5 hours later. The stomachs were removed and treated with formalin, and individual ulcers formed in the glandular portion of the stomach were measured in length (mm), with the measured ulcer lengths being summed for each rat. The test compound, suspended in a 0.5% aqueous solution of sodium carboxymethylcellulose, was given to the test group orally at a dose of 10 ml/kg body weight 30 min before the water-soaking constraint, whereas the vehicle alone was applied to a control group. The results are shown in Table 5.

Rats of KBL Wistar strain (weighing about 20 g), divided into groups each consisting of 3 heads, were treated through oral administration of the test compound suspended in powder gum arabic, followed by observation for any abnormalities over a 7 day period to find the number of dead animals. As a result, TTZ at doses up to 5,000 mg/kg did not cause any animal to die, thus leading to confirmation that the compound of the present invention shows an extremely enhanced degree of safety in contrast with its effective doses. The results are shown in Table 6.

TABLE 6

| Test compound | Dose (mg/kg) | Nd/No* |
|---|---|---|
| TTZ | 1,250 | 0/3 |
|  | 2,500 | 0/3 |
|  | 5,000 | 0/3 |
| FTZ | 1,250 | 0/3 |

TABLE 5

| Test compound | Dose (mg/kg) | Incidence of ulcer | Ulcer coefficient (mm) mean ± S.E. | Suppression % | $UD_{50}$ (mg/kg) (95% C.L.) |
|---|---|---|---|---|---|
| Vehicle (No. 1) | — | 8/8 | 31.9 ± 4.1 | — | |
| Vehicle (No. 2) | — | 8/8 | 22.9 ± 4.4 | — | |
| Vehicle (No. 3) | — | 8/8 | 34.7 ± 3.7 | — | |
| TTZ | 50 | 8/8 | 19.9 ± 4.6 | 37.6[a] | |
|  | 100 | 8/8 | 9.8 ± 2.3* | 57.2[b] | 72.8 |
|  | 150 | 8/8 | 7.6 ± 1.4** | 78.1[c] | (69.1–76.7) |
| FTZ | 50 | 8/8 | 28.5 ± 4.6 | 10.7[a] | |
|  | 100 | 8/8 | 14.4 ± 3.2 | 37.1[b] | 146.9 |
|  | 150 | 8/8 | 17.9 ± 3.2** | 48.4[c] | (139.0–155.2) |

Notes:
[a] Suppression in Vehicle No. 1.
[b] Suppression in Vehicle No. 2.
[c] Suppression in Vehicle No. 3
*Level of significance, p < 0.01.
**Level of significance, p < 0.01.

The above results indicate that TTZ, or the compound of this invention, exhibits improved suppressory activity in the antiulcer test, as compared with FTZ used as a control.

4. Acute toxicity test:

TABLE 6-continued

| Test compound | Dose (mg/kg) | Nd/No* |
|---|---|---|
| | 2,500 | 0/3 |
| | 5,000 | 0/3 |

Note
*Nd = No. of dead animals; No = Total No. of

Industrial Applicability

The novel 2-aminoethanesulfonic acid zinc complex compound of the present invention, in the anti-hepatitis test, can produce an improved effect as compared with 2-aminoethanesulfonic acid, glutathione and glycyrrhizin that were known, and also possesses an action to strengthen the hepatic detoxification effects against a great variety of compounds, such as a potent protective effect against the lethal toxicity of acetaldehyde, a metabolite of ethanol. Furthermore, the novel 2-aminoethanesulfonic acid zinc complex compound showed markedly distinct suppressory activity in the anti-ulcer test, while in the toxicity test, it was also confirmed to show an increased degree of safety. Consequently, the present invention can provide a novel medicinal drug that can exhibit anti-hepatitis activity, liver function improving activity and anti-ulcer activity in combination.

We claim:

1. The 2-aminoethanesulfonic acid zinc complex compound as represented by the formula:

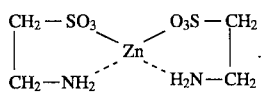

2. A process for producing the 2-aminoethanesulfonic acid zinc complex compound as represented by the formula:

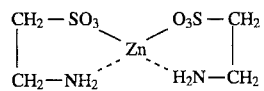

which comprises reacting a zinc compound with an alkali metal 2-aminoethanesulfonate.

3. A pharmaceutical composition comprised of a therapeutically effective amount of the compound of claim 1 and a pharmaceutically acceptable carrier.

4. The pharmaceutical composition of claim 3 which is an anti-hepatitis agent, liver function improving agent and anti-ulcer agent and which contain as an active ingredient the 2-aminoethanesulfonic acid zinc complex compound as represented by the formula:

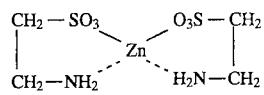

5. A method of improving the liver function activity of a patient in need of such treatment which comprises administering to said patient a liver function improving amount of a pharmaceutical composition comprised of a therapeutically effective amount of the compound of the formula:

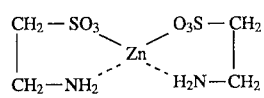

and a pharmaceutically acceptable carrier.

6. A method for treating ulcers in a patient which comprises administering to said patient a therapeutically effective amount of a pharmaceutical composition comprised of a therapeutically effective amount of the compound of the formula:

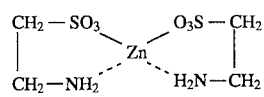

and a pharmaceutically acceptable carrier.

* * * * *